US00PP27967P2

(12) United States Plant Patent
Fitzgerald

(10) Patent No.: US PP27,967 P2
(45) Date of Patent: May 2, 2017

(54) ***CAREX* PLANT NAMED 'FICRE'**

(50) Latin Name: *Carex oshimensis*
Varietal Denomination: Ficre

(71) Applicant: Garraith Ltd, Old Town (IR)

(72) Inventor: Pat Fitzgerald, Old Town (IE)

(73) Assignee: GARRAITH LTD., Stoneyford, Oldtown (IE)

( * ) Notice: Subject to any disclaimer, the term of this patent is extended or adjusted under 35 U.S.C. 154(b) by 4 days.

(21) Appl. No.: 14/756,519

(22) Filed: Sep. 14, 2015

(51) Int. Cl.
*A01H 5/00* (2006.01)

(52) U.S. Cl.
USPC ..... Plt./384

(58) Field of Classification Search
USPC ..... Plt./384, 373
See application file for complete search history.

(56) References Cited

PUBLICATIONS

Upov Pluto Plant Variety Database Nov. 8, 2016 retrieved on Nov. 8, 2016 for Cares 'Evercream', retrieved from the Internet at <https://www3.wipo.int/pluto/user/en/index.jsp> one page.*

* cited by examiner

*Primary Examiner* — June Hwu
(74) *Attorney, Agent, or Firm* — Penny J. Aguirre

(57) ABSTRACT

A new cultivar of *Carex oshimensis*, 'Ficre', characterized its dwarf plant habit, its foliage that is variegated with deep green centers and creamy yellow margins, and its ust growth habit.

2 Drawing Sheets

Botanical classification: *Carex oshimensis.*
Varietal denomination: 'Ficre'.

BACKGROUND OF THE INVENTION

The present invention relates to a new and distinct cultivar of *Carex oshimensis* and will be referred to hereafter by its cultivar name, 'Ficre'. 'Ficre' is a new cultivar of perennial ornamental grass grown for container and landscape use, primarily in shaded exposures.

The new cultivar, 'Ficre' arose as a naturally occurring chimeral mutation of *Carex oshimensis* 'Evergold' (not patented). The Inventor discovered 'Ficre' in August of 2011 in a container at his nursery in Oldtown, Stoneyford, Co. Kilkenny, Republic of Ireland.

Asexual propagation of the new cultivar was first accomplished by shoot division in Oldtown, Stoneyford, Co. Kilkenny, Republic shoot division has determined that the characteristics are stable and are reproduced true to type in successive generations.

SUMMARY OF THE INVENTION

The following traits have been repeatedly observed and represent the characteristics of the new cultivar. These attributes in combination distinguish 'Ficre' as a distinct cultivar of *Carex.*

1. 'Ficre' exhibits a dwarf plant habit.
2. 'Ficre' exhibits foliage that is variegated with deep green centers and creamy yellow margins.
3. 'Ficre' exhibits a robust growth habit.

'Evergold', the parent plant of 'Ficre', differs from 'Ficre' in having foliage that is variegated with creamy yellow centers and green margins. 'Ficre' can be most closely compared to the cultivars 'Eversheen' (U.S. Plant Pat. No. 25,938) and 'Everlime' (U.S. Plant Pat. No. 25,622). 'Eversheen' differs from 'Ficre' in having foliage that is variegated with green-yellow centers and deep green margins. 'Everlime' differs from 'Ficre' in having variegated foliage with centers that are green in color with lime green margins.

BRIEF DESCRIPTION OF THE DRAWINGS

The accompanying colored photographs illustrate the overall appearance and distinct characteristics of a six month-old plant the new *Carex* as grown outdoors in a 19-cm container in Oldtown, Stoneyford, C. Kilkenny, Ireland.

The photograph in FIG. 1 illustrates the dwarf plant habit and appearance of 'Ficre' in bloom.

Figure 1:
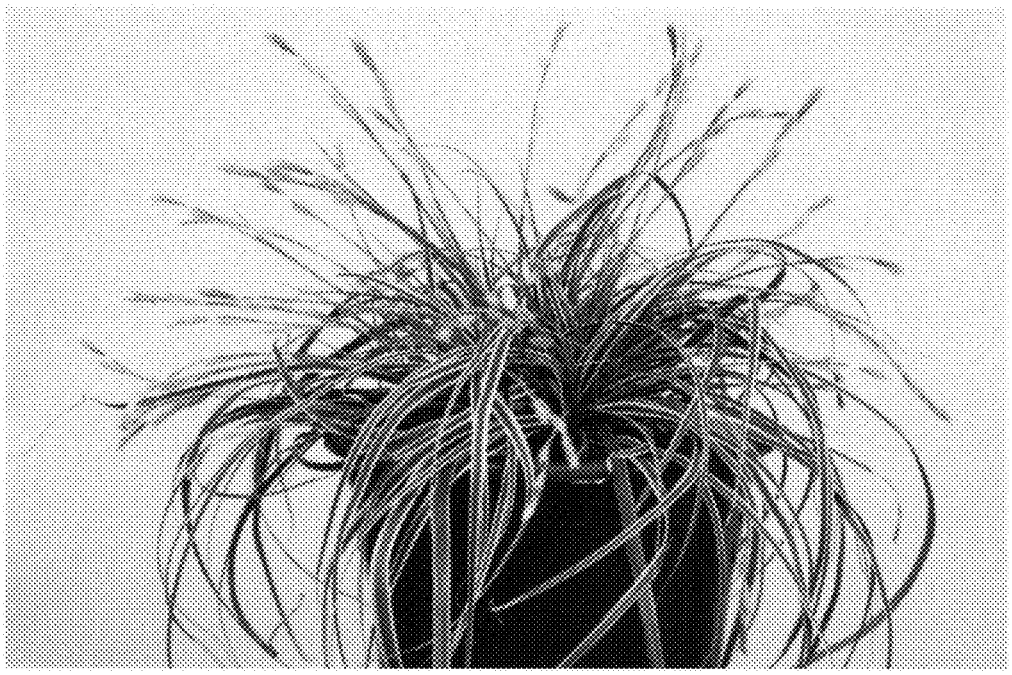
Figure 2:
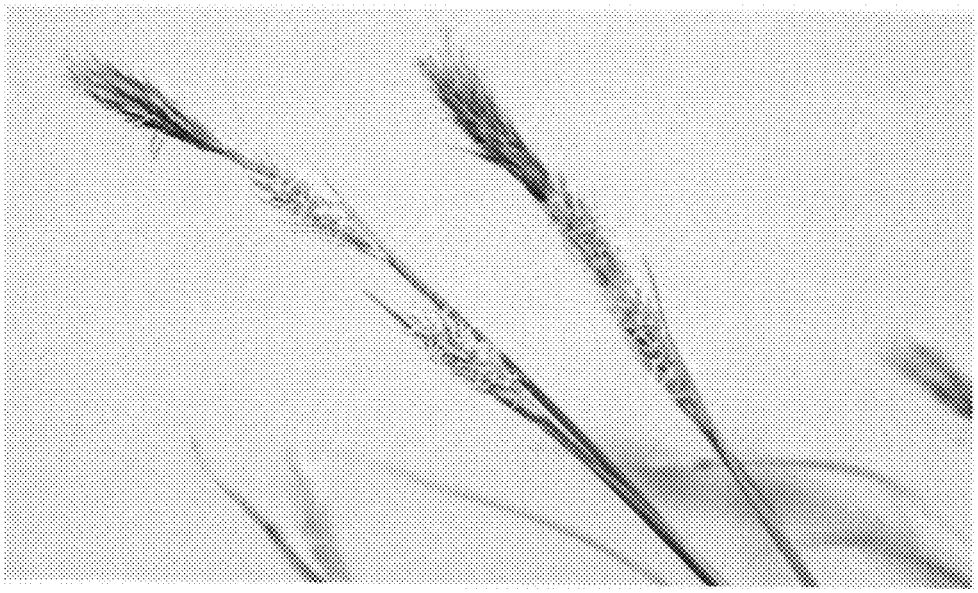

The photograph in FIG. 2 provides a close-up view of the flowers of 'Ficre'.

Figure 3:
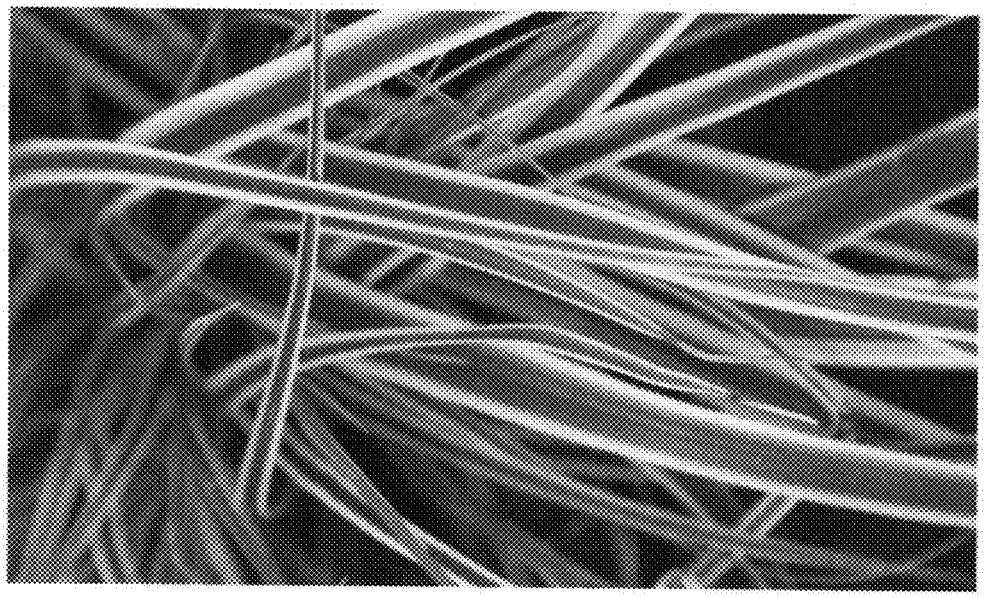

The photograph in FIG. 3 provides a close-up view of the foliage of 'Ficre'.

The colors in the photograph may differ slightly from the color values cited in the detailed botanical description, which accurately describe the colors of the new *Carex.*

DETAILED BOTANICAL DESCRIPTION

The following is a detailed description of six month-old plants as grown outdoors in a nursery in 19-cm containers in Co. Kilkenny, Republic of Ireland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Inflorescences emerge in mid February and continue into mid summer in the Republic of Ireland.

*Plant habit*.—Herbaceous perennial, flattened globular with arching leaves and inflorescences.

*Growth habit*.—Broad, spreading.

*Height and spread*.—Reaches about 19.7 cm in height, spreads to about 37.5 cm in diameter.

*Hardiness*.—At least in U.S.D.A. Zones 6.

*Plant vigor*.—Robust.

*Diseases and pests*.—No more susceptible or resistant to pests and diseases than other *Carex* varieties (which are typically dieseae free).

*Root description*.—Short, stout rhizomes with dense, fibrous roots, roots moderately branched.

*Propagation*.—Shoot division.

*Branching*.—Average of 62 main shoots grow from the base, no lateral branches.

Foliage description:

*Leaf shape*.—Linear, strongly curved (arching).

*Leaf division*.—Simple.

*Leaf base*.—Sheathing.

*Leaf apex*.—Long acuminate.

*Leaf aspect*.—Leaves initially emerge upright, then cascade outward and finally arch downward until the terminal blades lay on the ground.

*Leaf venation*.—Parallel.

*Leaf margins*.—Entire and moderately sharp when rubbed downwards due to very small teeth too small to be seen or measured.

*Leaf size*.—Matures to an average of 24.3 cm in length and 7 mm in width.

*Leaf number*.—Average of 10 leaves per shoot.

*Leaf arrangement*.—Alternate.

*Leaf surface*.—Upper side glossy, lower side moderately glossy, both sides are smooth.

*Leaf color*.—Young upper surface; 143A to 144A, with narrow margins 154C, young lower surface; 154C to 154D, mature upper surface; color between N137A and 139A, with margins 154D, mature lower surface; N137B with margins 154C to 154D.

*Durability to stresses*.—High.

*Petiole*.—No petioles, leaves sheathing; average of 1.9 cm in width and ranging between 177B to 177C and 201A to 201B in color.

Flower description:

*General description*.—Terminal racemes, male and female flowers on separate spikelets.

*Inflorescence size*.—Average of 6.1 cm in height and 9 mm in width.

*Flower quantity per inflorescence*.—Average of 45 male flowers placed in an average of 1 spikelet and an average of 72 female flowers placed in an average of 2 spikelets.

*Lastingness of inflorescence*.—Flowers last about 10 days.

*Flowering season*.—Continuous from late winter into summer.

*Response time to flower*.—Approximately 8 months.

*Rate of flower opening*.—After first initial flowers open in an inflorescence all flowers open within 3 weeks.

*Fragrance*.—None.

*Flower buds*.—Male flower: average of 5 mm in length and 2 mm in diameter, narrow oblong in shape and 199B to 199C in color, female flower: average of 5 mm in length and 2 mm in width, narrow obovate in shape and 147D in color.

*Spikelet shape*.—Sedge-like, narrowly ovate.

*Persistence of spikelets*.—Persistant.

*Floret (spikelet) size*.—Staminate florets; an average of 2 mm in diameter and 7 mm in length, pistillate florets; an average of 3 mm in diameter and 6 mm in length.

*Floret (spikelet) description*.—1 glume on inner side and 1 lemma on outer side, male flower: average of 1 glume and 1 lemma, glume and lemma surfaces smooth and dull, glume and lemma lanceolate in shape, glume and lemma entire margin, glume apex long, narrow and acute, lemma apex long and mucronate, glume and lemma 7 mm in length and 1 mm in width, glume and lemma color: upper and lower surface when opening and fully open; N199C to N199D, female flower: (no glume), lemma; 1, smooth and dull surfaces, lanceolate in shape, entire margin, apex long and mucronate, average of 6 mm in length and 1 mm in width, color: upper and lower surface when opening and fully open; 147D, margins tinged with 176B.

*Peduncle*.—An average of 15.2 cm in length and 1 mm in diameter, held upright to 5° to upright, glabrous surface, strong and 143A in color.

Reproductive organs:

*Gynoecium*.—Average of 1 pistil about 3 mm in length, stigma is fimbriate and 156D in color, style is about 0.5 mm in length and 144B in color, ovary is 144C in color.

*Androcoecium*.—Average of 3 stamens, basifixed, about 2 mm in length and 162A to 162B in color, pollen production very low and insufficient in quantity to be color coded.

*Fruits and seeds*.—Seed production has not been observed to date.

It is claimed:

1. A new and distinct cultivar of *Carex* plant named 'Ficre' as herein illustrated and described.

* * * * *